United States Patent
Nowakowski

[11] Patent Number: 6,155,977
[45] Date of Patent: Dec. 5, 2000

[54] METHOD AND APPARATUS FOR PLACEMENT OF A CATHETER

[76] Inventor: Bogdan Nowakowski, 2544 N. 65th Ave., Omaha, Nebr. 68104

[21] Appl. No.: 09/311,177

[22] Filed: May 13, 1999

[51] Int. Cl.[7] .................................................. A61B 5/00
[52] U.S. Cl. ........................................... 600/309; 604/192
[58] Field of Search ........................... 604/192; 600/309, 600/342, 343, 361, 350

[56] References Cited

U.S. PATENT DOCUMENTS

| | | | |
|---|---|---|---|
| 5,046,497 | 9/1991 | Millar ....................................... | 128/637 |
| 5,704,353 | 1/1998 | Kalb et al. ................................ | 128/634 |
| 5,788,631 | 8/1998 | Fiddian-Green ......................... | 600/309 |
| 5,928,155 | 9/1999 | Eggers et al. ............................ | 600/526 |

OTHER PUBLICATIONS

Digitrapper Mk III User's Manual Apr. 6, 1994 pp. 8–11 By Synectics Medical AB.

*Primary Examiner*—Sharon Kennedy
*Assistant Examiner*—Ann Y. Lam
*Attorney, Agent, or Firm*—Zarley, McKee, Thomte, Voorhees & Sease; Dennis L. Thomte

[57] ABSTRACT

The present invention provides a catheter which has an integral inflatable and deflatable balloon. The catheter includes an elongated, flexible tube and at least two spaced-apart openings therein. The operative element of the catheter is in communication with the first opening of the tube. The second opening in the catheter is in communication with the balloon. Preferably, the balloon is made of latex and extends around the diameter of the tube. Interfaces for both an inflation device for the balloon and a control device for the operative element are connected to the trailing end of the tube. The inflation device selectively inflates and deflates the balloon. The control device controls the operative element of the catheter. The catheter is placed by inserting the catheter with the balloon in a deflated position into the specified body channel. The body channel must have a restriction smaller than the size of the inflated balloon. The catheter is introduced into the body such that the deflated balloon passes through the restriction. At this point, the balloon is inflated. The catheter is then withdrawn until the balloon is in contact with the restriction. The balloon is then deflated and the catheter is in position. To ensure proper placement of the operative element of the catheter, the first opening must be an appropriate distance from the balloon.

11 Claims, 3 Drawing Sheets

METHOD AND APPARATUS FOR PLACEMENT OF A CATHETER

BACKGROUND OF THE INVENTION

1. Technical Field

This invention relates generally to the placement of a catheter in a human body and, more precisely, to the placement of a catheter within a channel in the human body with the channel having a restriction therein.

2. Description of the Prior Art

Catheters have been used by health care professionals for some time. They are generally used in the cardiopulmonary and gastrointestinal systems of the body due to the fact that these systems include channels into which the catheters are placed.

The catheters are used to introduce, measure, or extract fluids from the body. Particularly with regard to measuring the properties of the fluid of the body, proper placement of the catheter is of the utmost importance.

Proper placement of a catheter has been achieved by various means in the past Certain catheters have been equipped with miniature video camera capability. This allows the health care worker placing the catheter to see the position of the catheter with respect to the body. While accurate, this method has proven to be too expensive for many procedures.

Catheters have also been equipped with means for sensing ambient pressure for the purpose of proper placement. For example, Synectics Medical AB has developed a catheter, including a pressure sensing means, which is designed to be placed in the upper gastrointestinal tract of a body. The catheter is inserted into the nose of the patient and threaded into the stomach of the patient. The catheter is then extracted slowly. The stomach has comparatively lower ambient pressure than that of the lower esophagus. The pressure sensing means is connected to an external meter which shows the rise in ambient pressure. As the catheter is extracted, the pressure sensing means enters the esophagus and the pressure on the pressure sensing means rises. The catheter is then retained in this position.

The difference between the ambient pressure in the stomach and the ambient pressure in the esophagus may be very small, inhibiting accurate placement of the catheter. Also, the catheter must be extracted slowly. If the catheter is extracted too quickly, the catheter may be misplaced and may provide faulty data. Alternatively, the procedure may need to be repeated, causing discomfort to the patient. For these reasons, extensive training is required to place the existing catheters and, even with training, proper placement is difficult.

It is a primary objective of the present invention to provide a catheter which facilitates the proper placement thereof.

An additional objective is to provide a catheter that is inexpensive to build and inexpensive to use based, in part, on minimal training required to use it.

Another objective is to provide a catheter with an inflatable and deflatable balloon as a part thereof.

Another object of the invention is to teach a method of placing such a catheter precisely within a human body.

These and other objects will be apparent to those skilled in the art.

SUMMARY OF THE INVENTION

The catheter includes an elongated, flexible catheter tube having at least two spaced-apart openings therein, and an integral inflatable and deflatable balloon. The operative element of the catheter is in communication with the first opening of the tube. The operative element of the catheter may be a hollow tube positioned within the catheter tube for the introduction or withdrawal of fluids from the body through the first opening of the tube. The operative element may also be a meter or some other instrument by which body fluids are sampled. The upper end of the tube has an interface in communication with the operative element of the catheter, to which the means for operating the catheter is operatively connected. The second opening in the catheter is in communication with the inflatable and deflatable balloon. Preferably, the balloon is made of latex and extends around the diameter of the tube. The upper end of the tube includes means for inflating the balloon or a connection to such means. Such means may be a pump, vacuum, or remote meter for analyzing the properties of body fluids.

The catheter is placed by inserting the catheter with the balloon deflated into the specified body channel having a restriction smaller than the size of the inflated balloon. The inflatable and deflatable balloon is positioned on the tube with the interior thereof being in communication with the second opening in the tube. The catheter is introduced into the body such that the deflated balloon passes through the restriction, at which time the balloon is inflated. The catheter is then withdrawn until the balloon contacts or engages the restriction. The balloon is then deflated and the catheter is in position. To ensure proper placement of the operative element of the catheter, the first opening must be an appropriate distance from the balloon.

DESCRIPTION OF THE PREFERRED EMBODIMENT

Figure 1:
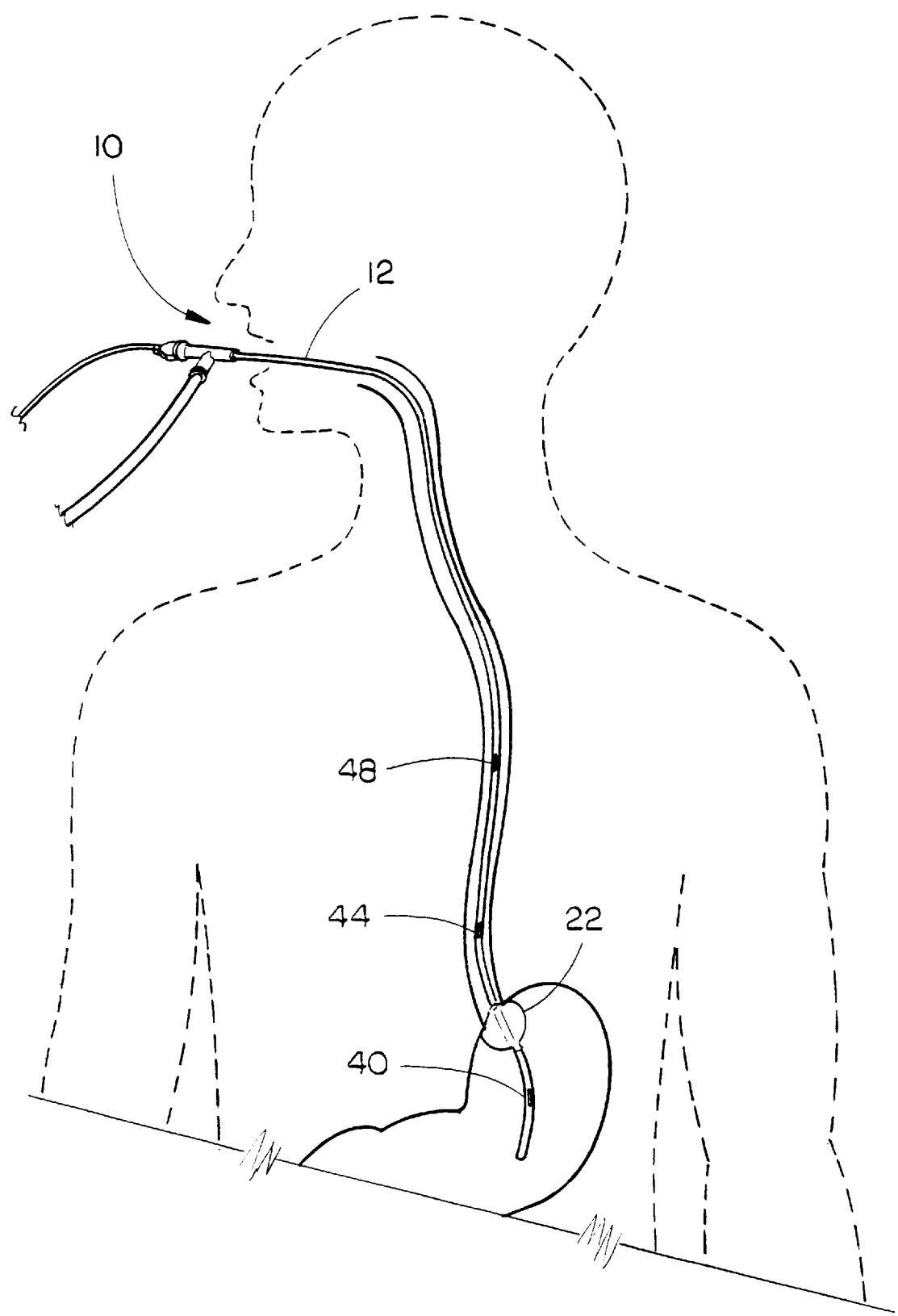
FIG. 1 is a view of the catheter in place in the gastrointestinal system of a human body.

Referring now to the drawings, the catheter of the present invention is designated generally by 10 and includes an elongated flexible tube 12. Tube 12 must be narrow enough to fit within the body channel for which it is designed. Tube 12 must also be long enough both to reach the area in which the catheter is designed to operate and to allow the trailing end 14 to extend from the body.

Tube 12 is provided with at least a first opening 16 and a second opening 18. An operative element, such as a sensing means 20, is positioned within and connected to the tube 12 such that an airtight seal is formed between the sensing means 20 and the tube 12 around the first opening 16. This structure exposes the sensing means 20 to the environment into which it is introduced and prevents the introduction of body fluids into the tube 12. The operative element may alternatively consist of a hollow tube for the withdrawal or introduction of fluids from the body. The exterior wall of the hollow tube must form an airtight seal with the wall of the tube 12 around the first opening 16 to allow fluids into the hollow tube, but not into the tube 12.

An inflatable and deflatable resilient balloon 22 is attached to the exterior of the tube 12, as seen in the drawings. Balloon 22 is, preferably, designed to circumscribe tube 12 about the second opening 18. Balloon 22 is connected to the tube 12 by a first annular seal 24 located between the second opening 18 and the leading end 26 of the tube 12. Balloon 22 is also connected to the tube 12 by a second annular seal 28 between the opening 18 and the trailing end 14 of the tube 12. Opening 16 must not be located between the first annular seal 24 and the second annular seal 28, because balloon 22 will prevent the exposure of sensing means 20 to the environment in which the catheter is placed.

Figure 2:
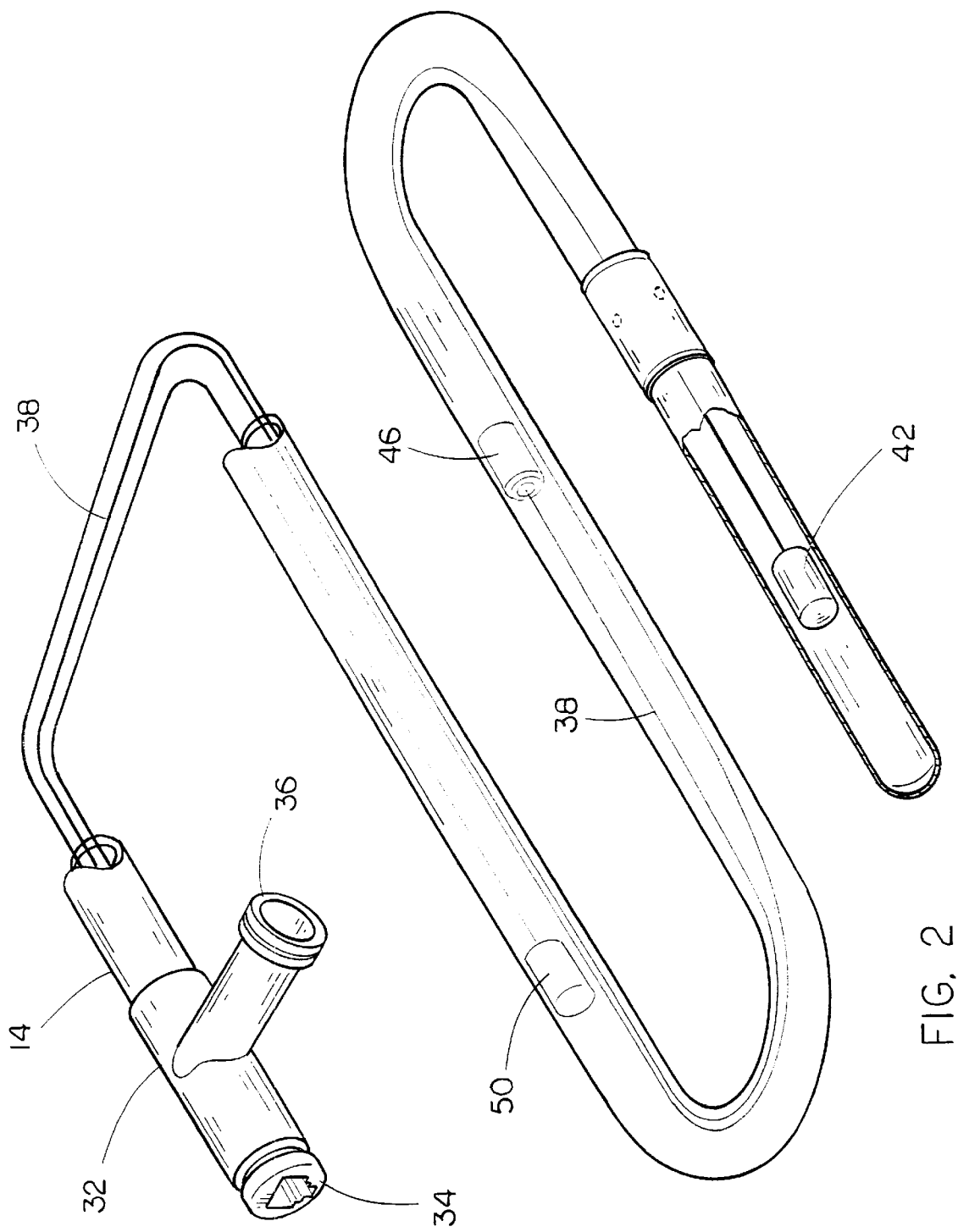
FIG. 2 is a perspective view of the catheter.
Figure 3:
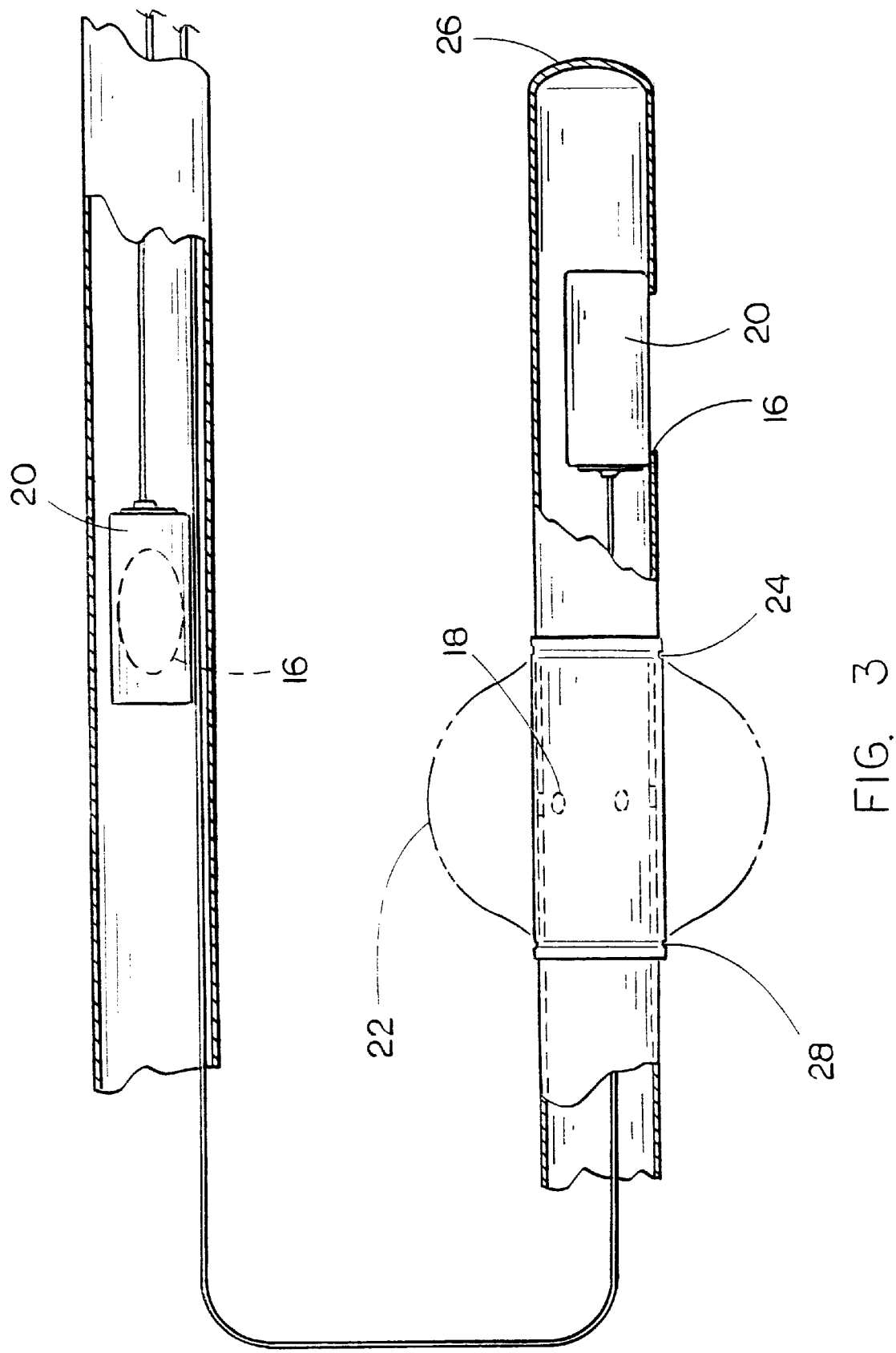
FIG. 3 is an exploded view of the catheter enlarged to show detail.

The trailing end 14 of the tube 12 is connected to a conventional means for operating catheter 10. As shown in FIG. 2, the trailing end 14 of tube 12 is connected to the means for operating catheter 10 by a T-shaped tubular junction 32. Other means are available to connect tube 12 to the means for operating catheter 10. The means for operating catheter 10 is comprised of an interface 34 for a control device to operate the sensing means 20 and an interface 36 for a conventional inflation device for inflating and deflating balloon 22. The interface 34 is in operative communication with the sensing means 20 by means of a conduit, such as relay 38. Where different operative elements are used, the conduit may be comprised of wires, tubes, or other media appropriate for the use of the control device.

Catheter 10 is used in the manner more fully described below. Leading end 26 of the catheter 10 is inserted into the appropriate body channel with the balloon 22 deflated. For proper placement, the body channel must have at least one restriction which is narrower than the balloon 22 after the balloon 22 has been inflated. Leading end 26 of the tube 12 is threaded through the body channel until second annular seal 28 passes through the channel restriction. An inflation device, not shown, is connected to the interface 36 as previously described and may consist of a pump, a syringe, or any other means of introduction of fluid. Interface 36 may be connected to the second opening 18 by means of a discrete tube, or, preferably, it may be connected directly to the tube 12 such that tube 12 and balloon 22 form a single airtight chamber.

The inflation device is activated to inflate balloon 22. While balloon 22 is still inflated, catheter 10 is withdrawn from the body until balloon 22 comes into contact with the restriction. First opening 16 must be located on the tube 12 at a specific distance from the balloon 22 for the intended purpose of the catheter 10. If, for instance, the user desires the sensing means 20 to be placed within the body 5 cm past the restriction in the body channel, opening 16 must be located between the balloon 22 and the leading end 26 of the tube 12 and 5 cm from the second annular seal 28. Similarly, if the operative element is designed to be placed in the body at a position between the orifice into which the catheter is placed and the restriction within the body channel, first opening 16 must be located between the balloon 22 and the trailing end 14. The distance between the balloon 22 and the first opening 16 will depend on the purpose for which the catheter 10 is used, the size of the body in which the catheter 10 is used, and other criteria.

More than one sensing means 20 may be used in conjunction with the catheter 10. Each or any of the sensing means 20 may be used to introduce, remove, or measure fluids in the body. In the embodiment shown in FIGS. 1 and 2, pH meters are accurately placed within the body by catheter 10. An opening 40 is located between the balloon 22 and the leading end 26 approximately 7 cm from the second annular seal 28. A first pH meter 42 is associated with the opening 40 and measures the pH of fluids in the stomach. An opening 44 is located between the balloon 22 and the trailing end 14 approximately 5 cm from second annular seal 28. A second pH meter 46 is associated with the opening 44 and measures the pH of fluids in the lower esophagus. An opening 48 is located between the balloon 22 and the trailing end 14 approximately 20 cm from the second annular seal 28. A third pH meter 50 is associated with the opening 48 and measures the pH of the fluids in the upper esophagus. Each pH meter is connected by a conduit 38; in this instance, a wire, to the control device interface 34, which is connected to a monitor or other device. Thus it can be seen that the invention accomplishes at least all of its stated objectives.

I claim:

1. A flexible catheter for placement in a body channel having a region to be monitored and a restriction of a given size therein, the restriction and the region being separated by a distance, comprising:

an elongated flexible tube having leading and trailing ends and at least first and second spaced-apart openings formed therein at a specified distance from each other;

sensing means disposed in said tube in communication with said first opening for collecting data;

conduit means positioned in said tube connected to said sensing means for the communication of data collected by sensing means;

a selectively inflatable and deflatable balloon affixed to said tube proximal said leading end and in communication with said second opening; said balloon being inflatable to a size larger than that of the restriction and being located a distance from said first opening equal to the distance between the restriction and the region of the body channel to be monitored; and said trailing end of said tube adapted to be connected to a means for inflating and deflating said balloon.

2. The flexible catheter of claim 1 wherein said tube includes additional spaced-apart openings formed therein, which are positioned at specified distances from each of said other openings, further comprising additional sensing means, each additional sensing means being in communication with and corresponding to an additional opening.

3. The flexible catheter of claim 2 wherein each of said additional sensing means is connected to a discrete conduit means, each of said discrete conduit means being housed within said tube.

4. The flexible catheter of claim 3 wherein said tube has an interior surface and said balloon has an interior surface; said interior surface of said tube and said interior surface of said balloon defining an airtight chamber.

5. The flexible catheter of claim 3 wherein each of said sensing means comprises a pH meter.

6. The flexible catheter of claim 1 wherein said sensing means comprises a pH meter.

7. A method of placing a catheter in a body channel having a restriction of a given size therein, comprising the steps of:

providing a catheter tube having spaced-apart first and second openings therein;

positioning a sensing means within said catheter tube so that said sensing means is in communication with said first opening;

positioning an inflatable and deflatable balloon on said catheter tube which is in communication with said second opening and which is spaced from said first opening a specified distance;

inserting said catheter into the body channel so that said balloon, in its deflated condition, passes through the restriction;

inflating said balloon to a size larger than the size of the restriction;

withdrawing said catheter from the body channel until said balloon contacts the restriction so that said sensing means is located at a specified distance from the restriction; and deflating said balloon.

8. A flexible catheter for placement in a body channel having a region in which fluids are to be transferred and a restriction of a given size therein, the restriction and the region being separated by a distance, comprising:

an elongated flexible catheter tube having leading and trailing ends and at least first and second spaced-apart openings at a specified distance from each other;

a conduit means comprising an elongated, hollow interior tube positioned in said catheter tube and having first and second ends, said interior tube first end in communication with said first opening, said interior tube second end positioned proximal said trailing end of said catheter tube for transfer of fluids through said interior tube between the trailing end of the catheter tube and the first opening therein;

a selectively inflatable and deflatable balloon affixed to said catheter tube proximal said leading end and in communication with said second opening; said balloon being inflatable to a size larger than that of the restriction and being located a distance from said first opening equal to the distance between the restriction and the region of the body channel region in which fluids are to be transferred; and said trailing end of said catheter adapted to be connected to means for inflating and deflating said balloon.

9. The flexible catheter of claim 8 wherein said catheter tube includes additional spaced-apart openings, formed therein which are positioned at specified distances from each of said other openings, further comprising additional elongated, hollow interior tubes, each additional interior tube having a first end in communication with and corresponding to an additional opening.

10. The flexible catheter of claim 9 wherein catheter tube has an interior surface and said balloon has an interior surface; said interior surface of said catheter tube, said interior surface of said balloon and said second opening defining an air tight chamber.

11. A method of placing a catheter in a body channel having a restriction of a given size therein and comprising the steps of:

providing a catheter tube having spaced-apart first therein;

positioning an elongated, hollow interior tube within said catheter tube, said interior tube having a first end positioned in communication with said first opening;

positioning an inflatable and deflatable balloon on said catheter tube which is in communication with said second opening and which is spaced from said first opening;

inserting said catheter into the body channel so that said balloon, in its deflated condition, passes through the restriction;

inflating said balloon to a size larger than the size of the restriction;

withdrawing said catheter from the body channel until said balloon contacts the restriction so that said first opening is located at a specified distance from the restriction; and deflating said balloon.

* * * * *